United States Patent [19]

Imai

[11] 4,179,469

[45] Dec. 18, 1979

[54] PREPARATION OF AMINES

[75] Inventor: Tamotsu Imai, Mt. Prospect, Ill.

[73] Assignee: UOP Inc., Des Plaines, Ill.

[21] Appl. No.: 971,285

[22] Filed: Dec. 20, 1978

[51] Int. Cl.$^2$ .............................................. C07C 85/18
[52] U.S. Cl. ................................. 260/577; 260/326.1; 260/563 R; 260/563 C; 260/570.8 R; 260/570.9; 260/583 R; 260/583 P; 260/576; 544/178; 544/410; 546/246; 548/325; 548/335; 548/371; 548/373; 548/262
[58] Field of Search ................... 260/563 R, 576, 577, 260/583 R, 585 D, 570.8, 570.9, 683.3

[56] References Cited

U.S. PATENT DOCUMENTS

| 2,422,632 | 6/1947 | Olin et al. ................. 260/563 R X |
| 2,497,310 | 2/1950 | Larson ................................. 260/585 |
| 3,446,865 | 5/1969 | Roth et al. ........................... 260/669 |
| 3,448,165 | 6/1969 | Bloch ................................ 260/683.3 |
| 3,513,200 | 5/1970 | Biale ..................................... 260/583 |
| 3,574,717 | 4/1971 | Lloyd .......................... 260/585 D X |
| 3,662,019 | 5/1972 | Stratenus ........................ 260/683.3 |
| 3,686,340 | 8/1972 | Patrick et al. ................... 260/672 R |
| 3,758,586 | 9/1973 | Coulson ........................... 260/583 R |
| 3,825,612 | 7/1974 | Wilhelm ........................... 260/668 D |
| 4,072,602 | 2/1978 | Hayes ................................. 208/138 |

FOREIGN PATENT DOCUMENTS 1909043  11/1970  Fed. Rep. of Germany ........ 260/683.3

*Primary Examiner*—John Doll
*Attorney, Agent, or Firm*—James R. Hoatson, Jr.; Raymond H. Nelson; William H. Page, II

[57] ABSTRACT

Amines, which may be utilized in various chemical processes, may be prepared in a combination process wherein the product mixture resulting from the dehydrogenation of a paraffin feed stock may be reacted with a nitrogen-containing compound, carbon monoxide and hydrogen, without separating the olefins in the product mixture, in the presence of certain catalytic compositions of matter to prepare the aforesaid amines.

18 Claims, 1 Drawing Figure

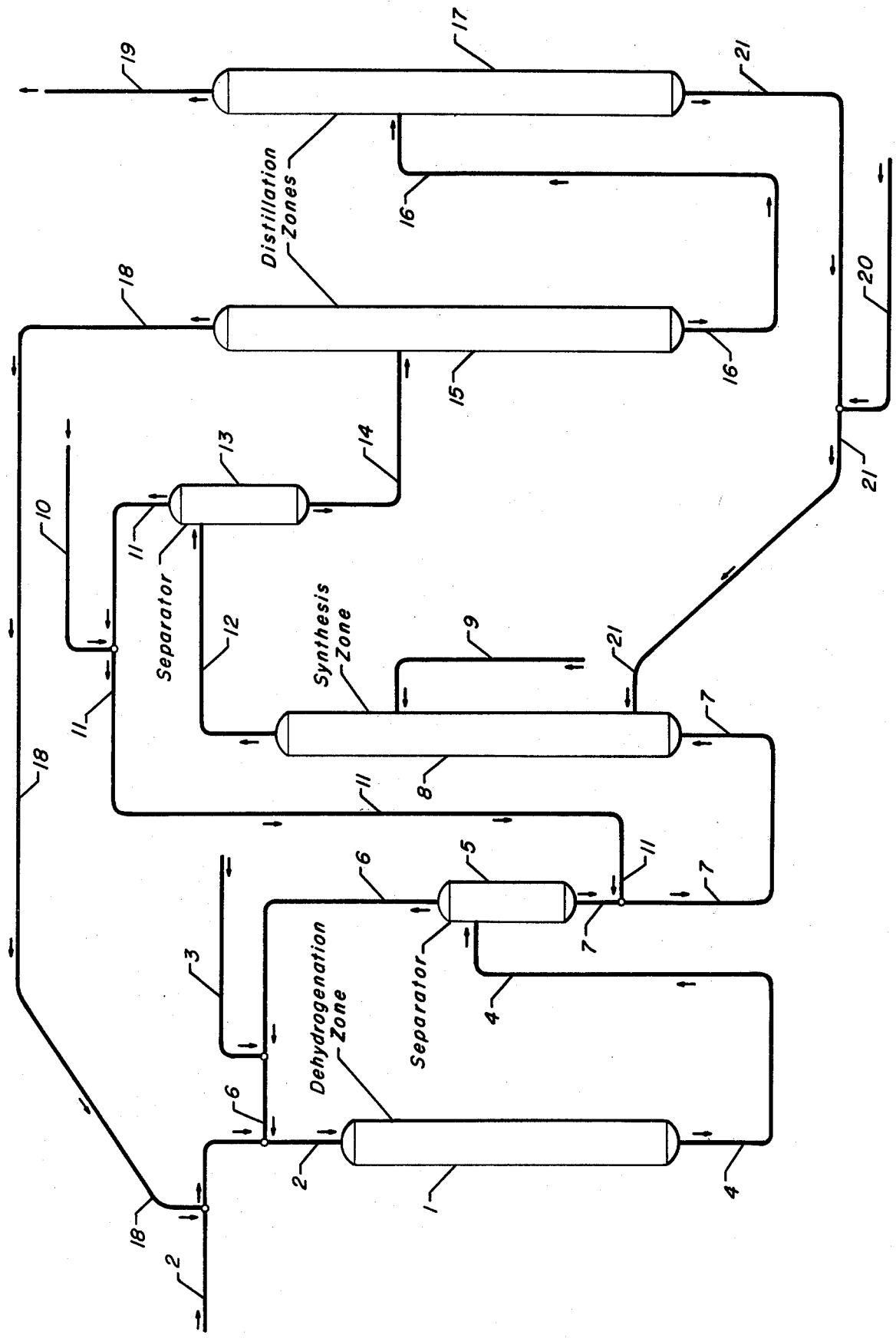

PREPARATION OF AMINES

BACKGROUND OF THE INVENTION

Heretofore amines have been prepared in a wide variety of reactions utilizing various metal-containing compounds as catalysts. For example, U.S. Pat. No. 3,091,641 discloses a process for preparing tertiary amines in which a secondary amine and an aliphatic ketone are reacted with carbon monoxide and water in the presence of an iron carbonyl catalyst such as iron pentacarbonyl or biscyclopentadienyl diiron tetracarbonyl. Another U.S. patent, namely, U.S. Pat. No. 2,497,310 discloses the synthesis of amines in which an unsaturated compound, carbon monoxide, hydrogen and ammonia or a substitute ammonia are reacted in the presence of a cobalt catalyst although other catalysts which possess hydrogenation properties such as nickel, ruthenium, iron and copper may also be used. Another prior art reference, namely, U.S. Pat. No. 3,947,458 is drawn to a process for preparing amines in which nitrogen-containing compounds and an olefin along with carbon monoxide and water are reacted in the presence of a catalyst comprising iron pentacarbonyl and a rhodium compound. In like manner, U.S. Pat. No. 3,234,283 also discloses a process for the preparation of trialkyl amines in which an olefin is reacted with carbon monoxide, hydrogen and a dialkyl amine in the presence of a catalyst consisting essentially of cobalt carbonyl trihydrocarbonphosphene. The hydrocarbon content of the catalyst is limited to trihydrocarbons containing a total of up to about 30 carbon atoms, the number of carbon atoms in any one of said hydrocarbon radicals not exceeding 18. Other prior art patents include U.S. Pat. No. 3,758,586 in which ethylene is reacted with secondary aliphatic amines in the presence of rhodium or iridium catalysts to form a tertiary amine in which one of the substituents is, of necessity, ethylene; U.S. Pat. No. 3,513,200 in which the preparation of tertiary amines is accomplished by reacting a secondary amine containing from 2 to about 20 carbon atoms with an aliphatic hydrocarbon olefin containing from about 2 to about 20 carbon atoms, as well as carbon monoxide and hydrogen in the presence of a complex catalyst comprising a Group VIII noble metal hydride in complex with a biphyllic ligand, said ligand containing phosphoric, arsenic or antimony; U.S. Pat. No. 3,412,158 which is drawn to a process for the preparation of aliphatic amines from the reaction of lower molecular weight olefins and ammonia, the primary product comprising a primary amine rather than a tertiary amine; U.S. Pat. No. 2,501,509 which is drawn to the preparation of amines by heating an ammonia type compound with a hydrocarbon olefinic compound utilizing an alkali metal catalyst such as sodium, this reference requires the presence of an organic liquid diluent for the olefinic reactant; and U.S. Pat. No. 2,422,631 in which aliphatic amines are produced by reacting an olefin, an oxide of carbon, hydrogen and an aminating agent in the presence of a hydrogenation-dehydration catalyst, examples of these catalysts being zinc chromate, zinc tungstate, chromium phosphate, cobalt oxide, iron oxide, etc.

In contradistinction to the above reactions, it will be hereinafter shown in greater detail that amines may be synthesized by utilizing, as one component in the reaction mixture, a feed stock consisting of the product mixture resulting from the dehydrogenation of dehydrogenatable hydrocarbons, said product mixture being utilized directly without separating the olefins resulting from the dehydrogenation of the dehydrogenatable hydrocarbons. By utilizing this product mixture as one component in the synthesis of amines, it is possible to significantly lower the cost of obtaining amines, thus rendering the process economically feasible to operate with a greater profit resulting to the processor.

As will also be hereinafter shown in greater detail, it is possible to effect the dehydrogenation of dehydrogenatable hydrocarbons utilizing certain catalytic compositions of matter whereby a greater yield of monoolefins, and particularly primary olefins, will be obtained.

SPECIFICATION

This invention relates to a process for the synthesis of amines. More specifically, the invention is concerned with a combination process for synthesizing amines in which a dehydrogenatable hydrocarbon is subjected to a hydrogenation stage in the presence of a nonacidic multimetallic catalyst. Thereafter the product mixture which results from this step of the process is utilized, without a separation of the olefins resulting from the dehydrogenation process, as one component of the amine synthesis reaction mixture. The product mixture is reacted with a nitrogen-containing compound, carbon monoxide and hydrogen in the presence of certain catalytic compositions of matter to obtain the desired product.

Amines will find a wide variety of uses in the chemical field. For example, the isomeric butylamines may be used as emulsifying agents, pharmaceuticals, insecticides, fungicides, dye-stuffs, etc.; dibutylamines may be used as corrosion inhibitors, rubber accelerators, dyes, etc., while tertiary amines may be used in agricultural applications, acting as an inert surfactant for herbicides; for use in corrosion inhibition and crude oil pipelines; in cosmetic formulation; leather processing; paint formulation; secondary oil recovery; mineral separation (cationic flocculation or flotation), etc. A specific compound, namely, tributylamine is used as a solvent, as an intermediate in the preparation of other chemicals and as an inhibitor in hydraulic fluids. In view of these important chemical uses, it is therefore necessary to effect the preparation of the amines in an economically feasible manner, said process requiring a relatively quantitative conversion of the olefins which are used in the process as well as requiring a high percentage of selectivity to the desired compound. These objectives may be attained by utilizing the process of the present invention in which the reaction is effected in the presence of certain catalytic compositions of matter of the type hereinafter set forth in greater detail.

It is therefore an object of this invention to provide a process for the synthesis of amines.

A further object of this invention is to provide a process for the synthesis of amines whereby economical, attractive yields of the desired product are obtained.

In one aspect an embodiment of this invention resides in a process for the peparation of an amine which comprises dehydrogenating a dehydrogenatable compound at dehydrogenating conditions in the presence of a dehydrogenating catalyst, treating the resultant product mixture in the absence of any separation with carbon monoxide, hydrogen and a nitrogen-containing compound in the presence of a catalyst comprising a rhodium- or ruthenium-containing compound at reaction conditions, and recovering the resultant amine.

A specific embodiment of this invention is found in a process for the preparation of amine which comprises dehydrogenating a normal paraffin containing from 2 to about 30 carbon atoms per molecule at a temperature in the range of from about 400° to about 700° C. and a pressure in the range of from about 1 to about 10 atmospheres in the presence of a nonacidic multimetallic catalyst comprising platinum, tin and/or rhenium and lithium composited on alumina, thereafter treating the resultant product mixture in the absence of any separation with carbon monoxide, hydrogen and dimethylamine at a temperature in the range of from about 50° to about 350° C. and a pressure in the range of from about 10 to about 300 atmospheres in the presence of rhodium chloride, and recovering the resultant amine.

Other objects and embodiments will be found in the following further detailed description of the present invention.

As hereinbefore set forth, the present invention is concerned with a process for synthesizing amines. These amines may be prepared utilizing a combination process in which the product mix resulting from the dehydrogenation of dehydrogenatable compounds may be utilized as the feed stock for reaction with a nitrogen-containing compound, carbon monoxide and hydrogen directly without separating the dehydrogenated hydrocarbons from said mix.

The dehydrogenation of the dehydrogenatable hydrocarbons is effected by contacting said hydrocarbons at dehydrogenation conditions with a nonacidic catalytic composite of a type hereinafter set forth in greater detail. Dehydrogenatable hydrocarbons which are utilized in the present process preferably comprise paraffinic hydrocarbons containing from about 2 to about 30 carbon atoms per molecule such as normal aliphatic hydrocarbons or cycloaliphatic hydrocarbons containing from about 4 to about 10 carbon atoms. The organic compound which is to undergo dehydrogenation will be capable of being dehydrogenated to produce products containing the same number of carbon atoms but fewer hydrogen atoms and which are capable of being vaporized at the dehydrogenation conditions which are utilized in the particular step of the process. Some specific examples of suitable dehydrogenatable hydrocarbons will include the aliphatic paraffins such as ethane, propane, n-butane, isobutane, n-pentane, isopentane, n-hexane, 2-methylpentane, 2,2-dimethylbutane, n-heptane, 2-methylhexane, 2,2-dimethylpentane, the isomeric octanes, nonanes, decanes, undecanes, dodecanes, tridecanes, tetradecanes, pentadecanes, hexadecanes, hexadecanes, heptadecanes, octadecanes, nonadecanes, eicosanes, henicosanes, docosanes, tricosanes, tetracosanes, pentacosanes, hexacosanes, heptacosanes, octacosanes, nonacosanes, triacontanes, etc.; naphthenes such as cyclobutane, cyclopentane, cyclohexane, methylcyclopentane, cycloheptane, ethylcyclopentane, methylcyclohexane, cyclooctane, 1,3-dimethylcyclohexane, isopropylcyclopentane, methylcycloheptane, etc. While the feedstream of the dehydrogenatable hydrocarbon may comprise one particular paraffinic or cycloparaffinic hydrocarbon, it is also contemplated that the feedstream may contain a mixture of 4 or 5 adjacent normal paraffin homologs such as $C_{10}-C_{13}$, $C_{11}-C_{14}$, $C_{11}-C_{15}$ and the like mixtures.

The dehydrogenation of the aforementioned dehydrogenatable hydrocarbons is effected in the presence of a nonacidic catalyst composite which contains a Group VIII noble metal and at least one element selected from Groups IA, IIA, IVA, VA and VIIB of the Periodic Table composited on a porous carrier material. These nonacidic multimetallic catalytic composites will possess improved activity, selectivity and stability characteristics. Examples of noble metals of Group VIII of the Periodic Table which comprise one component of the catalyst composite will preferably include platinum, palladium, iridium, etc. Examples of Group IA and IIA of the Periodic Table will include lithium, sodium, potassium, rubidium, cesium, magnesium, calcium, strontium, while elements of Groups IVA, VA and VIIB which may be employed will include in particular germanium, tin, lead, arsenic antimony, bismuth and rhenium. In a preferred embodiment, the nonacidic catalytic composite will contain, on an elemental basis, about 0.01 to about 2 wt. % of the noble metal of Group VIII, from about 0.01 to about 5 wt. % of the alkali or alkaline earth metal and from about 0.01 to about 5 wt. % of the Group IVA, VA and VIIB elements, said components being uniformly dispersed throughout the porous carrier material, wherein substantially all of the noble metal components are present in the corresponding elemental metallic states and wherein substantially all of the Group IVA, VA and VIIB component and the alkali or alkaline earth metal component are present in an oxidation state above that of the elemental metal.

As hereinbefore set forth, the multimetallic components are composited on a porous carrier material. It is preferred that this material be a porous, adsorptive, high surface area support having a surface area of about 25 to about 500 $m^2/g$. The porous carrier material should be relatively refractory to the conditions utilized in the dehydrogenation process and it is intended to include within the scope of the present invention carrier materials which have traditionally been utilized in hydrocarbon conversion catalysts such as: (1) activated carbon, coke or charcoal; (2) silica or silica gel, silicon carbide, clays and silicates including those synthetically prepared and naturally occurring, which may or may not be acid treated for example, attapulgus clay, china clay, diatomaceous earth, fuller's earth, kaolin, kieselguhr, etc.; (3) ceramics, procelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; and, (6) combination of elements from one or more of these groups. The preferred porous carrier materials for use in the present invention are refractory inorganic oxides, with best results obtained with an alumina carrier material. Suitable alumina materials are the crystalline aluminas known as the gamma-, eta- and theta-aluminas, with gamma-alumina giving best results. In addition, in some embodiments, the alumina carrier material may contain minor proportions of other well-known refractory inorganic oxides such as silica, zirconia, magnesia, etc.; however, the preferred support is substantially pure gamma-alumina. Preferred carrier materials have an apparent bulk density of about 0.2 to about 0.8 g/cc and surface area characteristic such that the average micropore diameter measured by nitrogen adsorption is about 20 to 300 Angstroms, the pore volume is about 0.1 to 1 cc/g and the surface area is about 10 to about 500 m$^2$/g. In general, excellent results are typically obtained with a gamma-alumina carrier material which is used in the form of spherical particles having: a relatively small diameter (i.e. typically about 1/16 inch), an apparent bulk density of about 0.3 g/cc, a pore volume of about 0.5 cc/g and a surface area of about 170 m$^2$/g.

The preferred alumina carrier material may be prepared in any suitable manner and may be prepared in a synthetic manner or may be naturally occurring. However, the alumina to be employed may be activated prior to use by one or more treatments including drying, calcination, steaming, etc. For example, the alumina carrier may be prepared by adding a suitable alkaline reagent, such as ammonium hydroxide, to a salt of alumina such as aluminum chloride in such an amount to form an aluminum hydroxide gel which, upon drying or calcining, is converted to alumina. The alumina carrier may be formed in any desired shape such as spheres, pills, cakes, extrudates, powders, granules, etc. A particularly preferred form of alumina is the sphere; and these spheres may be continuously manufactured by the well-known oil drop method which comprises the steps of: (1) forming an alumina hydrosol by any of the techniques taught in the art and preferably by reacting alumina metal with hydrochloric acid; (2) combining the resulting hydrosol with a suitable gelling agent; (3) and dropping the resultant mixture into an oil bath which is maintained at elevated temperatures. The droplets of the mixture remain in the oil bath until they set and form hydrogen spheres, said spheres then being continuously withdrawn from the oil bath and typically subjected to specific aging treatments in oil and an ammoniacal solution to further improve their physical characteristics. The resulting aged and gelled particles are then washed and dried at a relatively low temperature of from about 300° to about 400° F. followed by a calcination procedure at a temperature of about 850° to about 1300° F. for a period of from about 1 to about 20 hours. In the preferred procedure, the calcined particles are subjected to a high temperature treatment with steam in order to remove undesired acidic components such as any residual chloride. This method affects conversion of the alumina hydrogel to the corresponding crystalline gamma-alumina.

One component of the multimetallic catalyst comprises an element of Group IVA, VA and VIIB of the Periodic Table such as germanium, tin, arsenic, antimony, bismuth, rhenium, or lead. Substantially all of the Group IVA, VA and VIIB elements will be present in the final catalyst in an oxidation state above that of the elemental metal. This component may be present in chemical combination with one or more of the other ingredients of the composite, or as a chemical compound of germanium, tin or lead such as the oxide, sulfide, halide, oxyhalide, oxychloride, aluminate, etc., compounds, the preferred form of the compound being that of the corresponding oxide. This component is preferably present in the final composite in an amount in the range of from about 0.01 to about 5 wt. % thereof, calculated on an elemental basis, the most preferred amount being from about 0.05 to about 2 wt. %. This component may be incorporated in the composite in any suitable manner known in the art, the end result being in a uniform dispersion of the moiety throughout the carrier material, such as coprecipitation or cogellation with the porous carrier material, ion exchange with the carrier material or impregnation of the carrier material at any stage in its preparation. For example, one method of incorporating this component into the composite involves the utilization of a soluble decomposable compound of the Group IVA metal to impregnate the porous carrier material either before, during or after the carrier material is calcined. The solvent which is used during this impregnation step is selected on the basis of its capability to dissolve the desired compound without effecting the porous carrier material which is to be impregnated, good results being obtained when water is the solvent and thus the preferred compound for use in this impregnation step is typically water-soluble and decomposable. Regardless of which impregnation solution is utilized, the component may be impregnated either prior to, simultaneously with, or after the other metallic components are added to the carrier material.

A second metallic component of the multimetallic catalytic composite includes a noble metal of Group VIII of the Periodic Table such as platinum, palladium, ruthenium, rhodium, osmium or iridium. This component will generally comprise about 0.01 to about 2 wt. % of the final catalytic composite calculated on an elemental basis and the noble metal will exist within the final catalytic composite in the elemental metallic state. This component may also be incorporated in the catalytic composite in any suitable method known to result in a relatively uniform distribution of this component in the carrier material, said methods including coprecipitation, cogellation, ion exchange or impregnation. Again, as in the case of the Group IVA metal component of the catalyst, one method of preparing the composite involves the utilization of a soluble, decomposable compund to impregnate the carrier material in a relatively uniform manner. For example, as an illustration thereof this component may be added to the support by commingling said support with an aqueous solution of chloroplatinic or chloropalladic acid. Another method for incorporating this component into the catalytic composite comprises cogelling or coprecipitating the components such as iridium during the preparation of the carrier material. This is accomplished by the use of a soluble, decomposable compound of iridium such as chloroiridic acid or iridium tetrachloride to the alumina hydrosol before it is gelled. Thereafter the resulting mixture is then finished by conventional gelling, aging, drying and calcination steps.

Another component of the multimetallic catalytic composite which is utilized to dehydrogenate a dehydrogenatable hydrocarbon is a compound of Groups IA or IIA of the Periodic Table, that is, an alkali or alkaline earth component. In the preferred embodiment, this component is selected from the groups consisting of compounds of the alkali metals, namely, cesium, rubidium, potassium, sodium and lithium and of the alkaline earth metal, namely, calcium, strontium, barium and magnesium. This component exists within the catalytic composite in an oxidation state above that of the elemental metal such as a relatively stable compound including the oxide or sulfide, or in combination with one or more of the other components of the composite, or in combination with the carrier material such as for example, in the form of a metal aluminate. The amount of this component is preferably selected to provide a nonacidic composite containing from about 0.1 to about 5 wt. % of the alkali or alkaline earth metal, and more preferably, from about 0.25 to about 3.5 wt. %. In the preferred embodiment this component of the multimetallic catalyst composite will be a compound of lithium or potassium. The function of this component is to neutralize any of the acidic material which may have been used in the preparation of the catalyst in order to insure that the final catalyst composite is nonacidic in nature. Again, as in the case of the previously mentioned metallic components of the catalyst composite, the alkali or alkaline earth component may be combined with the porous carrier material in any manner known to those skilled in the art in order to result in a relatively uniform dispersion of this component throughout the carrier material with a subsequent neutralization of any acidic sites which may be present thereon. Best results are ordinarily obtained when this component is added to the carrier material in a step subsequent to the addition of the other metallic components inasmuch as the alkali metal or alkaline earth metal acts to neutralize the acid used in the preferred impregnation procedure for these metallic components. For example, the Group VIII noble metal component and the Group IVA noble metal component may be added to the carrier material and the resulting composite oxidized in a stream of air at a high temperature in the range of from about 600° to about 1000° F. following which the resulting oxidized component is treated with steam or a mixture of air and steam in order to remove at least a portion of any residual acidity, and thereafter add the alkali metal or alkaline earth metal component.

In the process of the present invention the dehydrogenatable hydrocarbon is contacted with a nonacidic multimetallic catalytic composite of the type hereinbefore set forth in greater detail in a dehydrogenation zone at dehydrogenating conditions. The contact of the hydrocarbon with the catalytic composite may be accomplished by using the catalyst in a fixed bed system, a moving bed system, a fluidized bed system or in a batch type operation. In the preferred embodiment the catalyst is disposed as a fixed bed in a dehydrogenation zone and a hydrocarbon feed stream which has been preheated by any suitable means to the desired reaction temperature is passed into said zone. It is, of course, understood that the dehydrogenation zone may be one or more separate reactors with suitable heating means therebetween to insure that the desired conversion temperature is maintained at the entrance to each reactor. The reactants may be contacted with the catalyst bed in either an upward, downward or radial flow phase and may be in the liquid phase, a mixed liquid-vapor phase or a vapor phase when in contact with the catalyst, the best results being obtained when utilizing a vapor phase reaction.

Although hydrogen is the preferred diluent for use in the reaction, it is also contemplated within the scope of this invention that other art-recognized diluents such as steam, methane, carbon dioxide and the like may also be advantageously utilized. In the preferred embodiment of the invention hydrogen is utilized due to the fact that it serves the dual function of not only lowering the partial pressure of the dehydrogenatable hydrocarbon, but also suppressing the formation of hydrogen-deficient, carbonaceous deposits on the catalytic composite. Ordinarily, hydrogen is utilized in amounts sufficient to insure a hydrogen to hydrocarbon mole ratio of about 1:1 to about 20:1, with best results obtained in the range of from about 1.5:1 to about 10:1. The hydrogen stream which is charged to the dehydrogenation zone will typically comprise recycle hydrogen which has been obtained from the effluent stream from the dehydrogenation zone after a suitable separation step. In addition, when hydrogen is used as the diluent, it is also contemplated that water or a water-producing compound be added to the dehydrogenation zone. This water additive may be included in the charge stock or in the hydrogen stream, or in both of these, or added independently. Ordinarily, it is preferred to inject the necessary water by saturating at least a portion of the input hydrogen stream with water. The amount of equivalent water which is added to the reaction zone should be of sufficient quantity to maintain the total amount of water continuously entering the dehydrogenation zone in a range of from about 50 to about 10,000 weight ppm. of the charge stock.

The reaction conditions or dehydrogenation conditions which are utilized are those which are generally selected from the conditions well known to those skilled in the art for the particular dehydrogenatable hydrocarbon which is charged to the zone. More specifically, suitable conversion temperatures are selected from the range of from about 400° to about 700° C., the particular temperature being dependent upon the dehydrogenatable hydrocarbon which comprises the feed stock. For example, temperatures within the lower portion of the range will be employed when subjecting the more easily dehydrogenated hydrocarbons such as long chain normal paraffins and from the higher portion of the range when subjecting the more difficultly dehydrogenated hydrocarbons to the process. In addition, the pressure which is utilized for the employment of this dehydrogenation process is ordinarily selected at a value which is as low as possible and yet consistent with the maintenance of catalyst stability. This pressure is usually in the range of from about 0.1 to about 10 atmospheres. The effluent stream which is recovered from the dehydrogenation zone will contain unconverted dehydrogenatable hydrocarbons as well as products of the dehydrogenation reaction and will, after being subjected to a cooling step, be passed into a second zone, without separating the unconverted hydrocarbons from the dehydrogenated hydrocarbons to a second zone wherein the synthesis of alkyl amines is effected. In this zone the product mixture will be contacted with carbon monoxide, hydrogen, and nitrogen-containing compounds of the type hereinafter set forth in greater detail, said amine synthesis being effected in the presence of certain catalytic compositions of matter comprising rhodium- or ruthenium-containing compounds.

The reaction conditions which are employed for effecting the synthesis of amines will include temperatures in the range of from about 50° to about 350° C. and pressures in the range of from about 10 to about 300 atmospheres. In the preferred embodiment of the invention, the pressures which are employed will be the autogeneous pressures resulting from the presence of carbon monoxide and hydrogen in the reaction mixture although it is also contemplated within the scope of this invention that the pressures resulting from the use of carbon monoxide and hydrogen will comprise only a partial operating pressure, the remainder being afforded by the introduction of a substantially inert gas such as nitrogen, helium, argon, etc., into the reaction vessel. Other reaction conditions which are present during the synthesis of amines will include mole ratios of the various components. For example, the carbon monoxide which is employed in the reaction mixture will be present in a mole ratio in the range of from about 1:1 to about 100:1 moles of carbon monoxide/mole of unsaturated hydrocarbon; 1:1 to about 3:1 moles of olefinic compound/mole of nitrogen-containing compound, said ratio being dependent upon the type of nitrogen-containing compound which is employed and whether a primary, secondary or tertiary amine is to be the desired product, and 0.5:1 to about 3:1 moles of hydrogen/mole of carbon monoxide.

Examples of nitrogen-containing compounds which may be utilized as one component of the reaction mixture for the synthesis of amine will include ammonia, primary amines such as methylamine, ethylamine, n-propylamine, isopropylamine, n-butylamine, t-butylamine, n-pentylamine, sec-pentylamine, the isomeric hexylamines, heptylamines, octylamines, nonylamines, decylamines, undecylamines, dodecylamines, tridecylamines, tetradecylamines, etc., aniline, o-toluidine, m-toluidine, p-toluidine, o-xylidine, m-xylidine, p-xylidine, 2-ethylaniline, 3-ethylaniline, 4-ethylaniline, 2-propylaniline, 3-propylaniline, 4-propylaniline, cyclopentylamine, cyclohexylamine, cycloheptylamine, cyclooctylamine, etc., secondary amines such as dimethylamine, diethylamine, di-n-propylamine, diisopropylamine, di-n-butylamine, di-t-butylamine, di-n-pentylamine, di-sec-pentylamine, the isomeric dihexylamines, diheptylamines, dioctylamines, dinonylamines, didecylamines, diundecylamines, didodecylamines, ditridecylamins, ditetradecylamines, etc., dianiline, di-o-toluidine, di-m-toluidine, di-p-toluidine, di-o-xylidine, di-m-xylidine, di-p-xylidine, di-2-ethylaniline, di-3-ethylaniline, di-4-ethylaniline, di-2-propylaniline, di-3-propylaniline, di-4-propylaniline, dicyclopentylamine, dicyclohexylamine, dicycloheptylamine, dicyclooctylamine, etc.; heterocyclic compounds such as pyrrole, pyrazole, imidazole, 1,2,3-triazole, 1,2,4-triazole, 2,1,3-triazole, 4,1,2-triazole, 1,2,3,4-tetrazole, 1,2,3-dioxazole, 1,3,2-dioxazole, 1,2,4-dioxazole, 1,3,4-dioxazole, 1,3,4,2-dioxadiazole, 1,2,3-dithiazole, 1,2,4-dithiazole, 1,3,2-dithiazole, 1,3,4-dithiazole, 1,3,2,4-dithiadiazole, piperazine, o-isoxazine, o-isothiazine, p-isoxazine, p-isothiozine, morpholine, isoindole, isoindazole, benzimidazole, indazole, 1,2,3-benzotriazole, 2,1,3-benzotriazole, 1,3,4,6-benzotetrazole, 4-aminomethylpiperidine, 4-aminoethylpiperidine, 4-aminopropylpiperidine, 4-aminomethylpyran, 4-aminoethylpyran, 4-aminomethylthiapyran, 4-aminoethylthiapyran, etc.; polyamines such as methylenediamine, ethylenediamine, propylenediamine, butylenediamine, amylenediamine, hexylenediamine, N,N'-dimethylethylenediamine, N,N'-dimethylpropylenediamine, N,N'-dimethylbutylenediamine, N,N'-dimethylamylenediamine, N,N'-dimethylhexylenediamine, N,N'-diethylethylenediamine, N,N'-diethylbutylenediamine, N,N'-diethylhexylenediamine, N,N'-dipropylmethylenediamine, N,N'-dipropylpropylenediamine, N,N'-dipropylamylenediamine, N,N'-dibutylethylenediamine, N,N'-dibutylpropylenediamine, N,N'-dibutylbutylenediamine, N,N'-dioctylethylenediamine, N,N'-dioctylbutylenediamine, N,N'-dioctylhexylenediamine, N,N'-didecylmethylenediamine, N,N'-didecylethylenediamine, N,N'-didecylpropylenediamine, N,N'-diphenylethylenediamine, N,N'-diphenylpropylenediamine, N,N'-diphenylbutylenediamine, N,N'-diphenylhexylenediamine, N,N'-dibenzylethylenediamine, N,N'-dibenzylpropylenediamine, N,N'-dibenzylbutylenediamine, N,N'-dicyclopentylethylenediamine, N,N'-dicyclopentylpropylenediamine, N,N'-dicyclopentylbutylenediamine, N,N'-dicyclohexylmethylenediamine, N,N'-dicyclohexylethylenediamine, N,N'-dicyclohexylhexylenediamine, N,N'-di(p-tolyl)ethylenediamine, N,N'-di-(p-tolyl)propylenediamine, diethylenetriamine, dipropylenetriamine, triethylenetetraamine, tripropylenetetraamine, N,N'-dimethyldiethylenetriamine, N,N'-diethyldiethylenetriamine, N,N'-dipropyldiethylenetriamine, N,N'-dipentyldiethylenetriamine, N,N'-dioctyldiethylenetriamine, N,N'-diphenyldiethylenetriamine, N,N'-dibenzyldiethylenetriamine, N,N'-dicyclopentyldiethylenetriamine, N,N'-dicyclohexyldiethylenetriamine, N,N'-di(p-tolyl)-diethylenetriamine, N,N'-dimethyltriethylenetetraamine, N,N'-diethyltriethylenetetraamine, N,N'-dipropyltriethylenetetraamine, N,N'-dipentyltriethylenetetraamine, N,N'-dioctyltriethylenetetraamine, N,N'-diphenyltriethylenetetraamine, N,N'-dibenzyltriethylenetetraamine, N,N'-dicyclopentyltriethylenetetraamine, N,N'-dicyclohexyltriethylenetetraamine, N,N'-di(p-tolyl)triethylenetetraamine, N,N'-dimethyldipropylenetriamine, N,N'-dipropyldipropylenetriamine, N,N'-dioctyldipropylenetriamine, N,N'-dibenzyldipropylenetriamine, N,N'-dicyclohexyldipropylenetriamine, N,N'-diethyltripropylenetetraamine, N,N'-dipentyltripropylenetetraamine, N,N'-diphenyltripropylenetetraamine, N,N'-dicyclopentyltripropylenetetraamine, N,N'-di(p-tolyl)tripropylenetetraamine, etc.

The synthesis of the amines by the reaction of the product mixture from a dehydrogenation zone, nitrogen-containing compound, carbon monoxide and hydrogen is effected in the presence of certain catalytic compositions of matter, said compositions comprising rhodium- or ruthenium-containing compounds. In the preferred embodiment of the invention, the ruthenium- or rhodium-containing compounds will comprise the metals or the nitrates, halides, halocarbonyls or carbonyl complexes. Specific examples of these compounds which are employed will include rhodium, rhodium nitrate, rhodium chloride, rhodium bromide, rhodium iodide, rhodium fluoride, chlorodicarbonylrhodium dimer, rhodium carbonyl, chlorobis(ethylene)rhodium dimer, ruthenium, ruthenium nitrate, ruthenium chloride, ruthenium bromide, ruthenium iodide, ruthenium fluoride, dichlorotricarbonylruthenium dimer, ruthenium carbonyl, etc.

BRIEF DESCRIPTION OF THE DRAWING

The present invention will be further illustrated with reference to the accompanying drawing which sets forth a flow diagram of the process of this invention. It is to be understood that various valves, pumps, etc., have been eliminated as not being essential to the complete understanding of the present invention. However, the utilization of these, as well as other similar appurtenances will become obvious as the drawing is described.

Referring now to the drawing, a charge stock comprising a dehydrogenatable hydrocarbon or a mixture of dehydrogenatable hydrocarbons is charged to dehydrogenation zone 1 through line 2. Dehydrogenation zone 1 contains a catalyst of the type hereinbefore set forth in greater detail, the catalyst preferably being positioned in the zone in the form of a fixed bed. In addition, a stream of hydrogen may also be charged to dehydrogenation zone 1 through line 3. In dehydrogenation zone 1 the dehydrogenatable hydrocarbons are contacted with the catalyst at dehydrogenation conditions which include a temperature in the range of from about 400° to about 700° C. and a pressure in the range of from about 0.1 to about 10 atmospheres, the reaction parameters being dependent upon the particular hydrocarbon which is to undergo dehydrogenation. After passage through dehydrogenation zone 1, the effluent is withdrawn through line 4 and passed to gas/liquid separator 5. The hydrogen which is stripped from the reaction product is withdrawn through line 6 and recycled back to dehydrogenation zone 1. The product mixture containing dehydrogenatable hydrocarbons such as paraffins along with the reaction product comprising olefins is withdrawn from gas/liquid separator 5 through line 7 and passed to synthesis zone 8. This zone also contains a catalyst of the type hereinbefore set forth, that is, a rhodium- or ruthenium-containing compound, said catalyst also being positioned in synthesis zone 8 in the form of a fixed bed. In synthesis zone 8 the product mixture is contacted with a nitrogen-containing compound which is charged to zone 8 through line 9 as well as a mixture of carbon monoxide and hydrogen which is charged through lines 10 and 11. As shown in the drawing, the carbon monoxide and hydrogen are admixed with the product mixture from gas/liquid separator 5 prior to entry into synthesis zone 8 although, if so desired, the aforesaid blend gas mixture of carbon monoxide and hydrogen may be charged directly to synthesis zone 8. In synthesis zone 8 which is maintained at the reaction conditions which include a temperature in the range of from about 50° to about 350° C. and a pressure in the range of from about 10 to about 300 atmospheres, the synthesis of the amine will occur. The effluent from synthesis zone 8 is withdrawn through line 12 and passed to a second gas/liquid separator 13 wherein any unreacted carbon monoxide and hydrogen are separated from the liquid and recycled through line 11 back to synthesis zone 8. The reaction mixture comprising amines, dehydrogenatable hydrocarbons such as paraffins and unreacted olefins are withdrawn from separator 13 through line 14 and passed to a first distillation zone 15. In distillation zone 15 the amines which comprise the desired product of the process along with any catalyst complex which may have also been removed from synthesis zone 8 are withdrawn through line 16 and passed to second distillation zone 17. The unreacted dehydrogenatable hydrocarbons and olefins are withdrawn from distillation zone 15 through line 18 and recycled back to line 2 where they are admixed with fresh dehydrogenatable hydrocarbon feed and charged to dehydrogenation zone 1. In the second distillation zone 17, the amines are separated from any catalyst and withdrawn through line 19 for storage. The catalyst complex which has been separated from the amines is withdrawn from distillation zone 17 through line 19 and recharged to synthesis zone 8. In addition, any makeup catalyst may be added to line 21 through line 20 and the mixture then charged to synthesis zone 8.

It is to be understood, of course, that variations and modifications may be made to the illustrated flow scheme without necessarily departing from the scope of the invention.

Examples of amines which may be prepared according to the process of this invention will include propylamine, the isomeric butylamines, pentylamines, hexylamines, heptylamines, octylamines, nonylamines, decylamines, undecylamines, dodecylamines, tridecylamines, tetradecylamines, pentadecylamines, hexadecylamines, heptadecylamines, octadecylamines, nonadecylamines, eicosylamines, docosylamines, etc., dipropylamine, the isomeric dibutylamines, dipentylamines, dihexylamines, diheptylamines, dioctylamines, dinonylamines, didecylamines, diundecylamines, didodecylamines, dioctadecylamines, didocosylamines, etc., propyldimethylamine, butyldimethylamine, hexyldimethylamine, octyldimethylamine, dodecyldimethylamine, octadecyldimethylamine, docosyldimethylamine, propyldiethylamine, butyldiethylamine, hexyldiethylamine, octyldiethylamine, dodecyldiethylamine, octadecyldiethylamine, docosyldiethylamine, phenyldiethylamine, phenyldipropylamine, cyclohexyldipropylamine, cyclohexyldidodecylamine, hexyldiphenylamine, dodecyldiphenylamine, undecyldicyclohexylamine, octadi(p-tolyl)amine, decyldi(p-tolyl)-amine, N-propylmorpholine, N-butylmorpholine, N-amylmorpholine, N-octylmorpholine, N-dodecylmorpholine, N-hexadecylmorpholine, N-eicosylmorpholine, N-docosylmorpholine, N-amylpyrrole, N-octylpyrrole, N-dodecylpyrrole, N-tetradecylpyrrole, N-docosylpyrrole, N-propylpiperidine, N-butylpiperidine, N-octylpiperidne, N-dodecylpiperidine, N-hexadecylpiperidine, N-propyl-1,2,4-triazole, N-butyl-1,2,4-triazole, N-dodecyl-1,2,4-triazole, N-docosyl-1,2,4-triazole, 1-propyl-4-dipropylaminomethylpiperidine, 1-hexyl-4-dipropylaminomethylpiperidine, 1-octyl-4-dipropylaminomethylpiperidine, 1-dodecyl-4-dipropylaminomethylpiperidine, 1-tetradecyl-4-dipropylaminomethylpiperidine, 1-docosyl-4-dipropylaminomethylpiperidine, etc., N,N,N',N'-tetraethylethylenediamine, N,N,N',N'-tetrapropylethylenediamine, N,N,N',N'-tetrapentylethylenediamine, N,N,N',N'-tetraoctylethylenediamine, N,N,N',N'-tetradodecylethylenediamine, N,N,N',N'-tetratridecylethylenediamine, N,N,N',N'-tetratricosylethylenediamine, N,N,N',N'-tetrabutylpropylenediamine, N,N,N',N'-tetradecylpropylenediamine, N,N,N',N'-tetrapropylbutylenediamine, N,N,N',N'-tetraoctylbutylenediamine, N,N,N',N'-tetradodecylbutylenediamine, N,N,N',N'-tetrapentylhexylenediamine, N,N,N',N'-tetradecylhexylenediamine, N,N,N',N'-tetradodecylhexylenediamine, N,N'-dimethyl-N,N'-dioctylethylenediamine, N,N'-dimethyl-N,N'-didodecylethylenediamine, N,N'-diphenyl-N,N'-di(tricosyl)ethylenediamine, N,N'-dicyclohexyl-N,N'-dioctylethylenediamine, N,N,N',N'-tetraoctyldiethylenetriamine, N,N,N',N'-tetradodecyldiethylenetriamine, N,N,N',N',N''-pentaoctyldiethylenetriamine, etc. It is to be understood that the aforesaid tertiary amines are only representative of the class of compounds which may be prepared according to the process described herein, and that the present invention is not necessarily limited thereto.

The following examples are given for purposes of illustrating the process of the present invention. However, it is to be understood that said examples are merely illustrative in nature and that the present process is not necessarily limited thereto.

EXAMPLE 1

A reactor was loaded with 6.0 grams of a nonacidic catalyst containing about 0.36 wt. % platinum, 0.5 wt. % tin, 0.55 wt. % lithium on an alumina basis, said catalyst having an ABD of 0.3. A feed stream comprising n-heptane was contacted with the catalyst at a temperature in the range of from about 500° to about 530° C., a pressure ranging from 10 to 30psig, and a liquid hourly space velocity ranging from 30 to 70 hr.$^{-1}$. In addition, hydrogen was also passed to the reactor in a range of from 4 to 8 moles of hydrogen/mole of n-heptane.

The hydrocarbon product stream from this reactor was then charged to a 300 cc rocking autoclave containing 0.022 grams of a rhodium chloride catalyst. The 50.15 grams of the hydrocarbon feed charge and 4.58 grams of dimethylamine were sealed into the autoclave and 150 atmospheres of a blend gas consisting of a 1:1 mole ratio of carbon monoxide to hydrogen was charged to the autoclave. The autoclave was then heated to a temperature of 150° C. and maintained at this temperature for a period of 3 hours. During this period the pressure in the autoclave dropped from 214 atmospheres to 212 atmospheres. At the end of the 3 hour period, heating was discontinued and the autoclave was allowed to return to room temperature. Upon reaching room temperature the excess pressure was discharged and the reaction mixture was recovered therefrom. Analysis of the product by means of gas liquid chromatography and elementary analyses showed that there had been a 100% conversion of the olefins with a 59% selectivity to octyldimethylamine.

EXAMPLE II

In a manner similar to that set forth in Example I above, 39.85 grams of hydrocarbon product feed resulting from the treatment of n-heptane over a nonacidic catalyst of the type set forth in Example I above at similar conditions along with 3.67 grams of dimethylamine and 0.018 grams of a rhodium chloride catalyst were placed in a 300 cc rocking autoclave. The autoclave was sealed and 150 atmospheres of a blend gas comprising a 4:1 mole ratio of carbon monoxide to hydrogen was charged thereto. The autoclave was then heated to a temperature of 150° C. and maintained at this temperature for a period of 3 hours, the pressure dropping from 195 atmospheres to 176 atmospheres during this time. Upon completion of the 3 hour time period heating was discontinued and the autoclave was allowed to return to room temperature. After reaching room temperature the excess pressure was discharged and the reaction mixture was recovered therefrom. The product was subjected to gas liquid chromatography and elementary analysis which disclosed that there had been a 100% conversion of the olefins in the hydrocarbon product stream with a 98% selectivity to octyldimethylamine.

EXAMPLE III

In this example an n-heptane charge which had been subjected to dehydrogenation in a manner similar to that set forth in Example I above and the product stream were recovered therefrom. In a 350 cc rotating autoclave was placed 0.015 grams of chlorodicarbonylrhodium dimer which acted as a catalyst for the reaction along with 50 grams of the product stream resulting from the dehydrogenation of n-heptane and 4.39 grams of dimethylamine. The autoclave was then sealed and 150 atmospheres of a blend gas comprising a 1:1 mole ratio of carbon monoxide/hydrogen was charged thereto. The autoclave was then heated to a temperature of 150° C. and maintained thereat for a period of 3 hours, the pressure dropping from 208 atmospheres to 205 atmospheres during this period. Upon completion of the 3 hour residence time heating was discontinued and after the autoclave had been allowed to return to room temperature the excess pressure was discharged. The reaction mixture was recovered therefrom and analysis of the product disclosed that there had been a 100% conversion of the olefins present in the product stream along with a 54% selectivity to octyldimethylamine.

When the above experiment was repeated utilizing 0.059 grams of a catalyst comprising trirhodium-dodecacarbonyl under similar conditions, analysis of the product by means of gas liquid chromatography and elementary analysis showed that there had been a 95.5% conversion of the olefins in the product stream with a 71% selectivity to octyldimethylamine.

EXAMPLE IV

In this example a reactor containing 6.0 grams of a catalyst similar in nature to that described in Example I above, was contacted with a paraffinic hydrocarbon containing a mixture of from $C_{11}$ to $C_{14}$ normal paraffins. The feed stream was contacted with the catalyst at a temperature in the range of from about 470° to 490° C., a pressure of 30 psig and a liquid hourly space velocity of from 20 to 30 hr.$^{-1}$. In addition, hydrogen was also charged to the reactor at a rate sufficient to maintain a molar ratio of 8 moles of hydrogen/mole of paraffin.

The hydrocarbon product stream was recovered from this reactor and 51.1 grams of said product stream was charged to a 350 cc rotating autoclave which contained 0.016 grams of a rhodium chloride catalyst and 1.184 grams of dimethylamine. The reactor was sealed and a 1:1 mole ratio of carbon monoxide/hydrogen blend gas was charged to the reactor until a pressure of 150 atmospheres was reached. The autoclave was then heated to a temperature of 150° C. and maintained thereat for a period of 3 hours. At the end of the 3 hour period, heating was discontinued and the autoclave was allowed to return to room temperature. The excess pressure was discharged, the autoclave was opened and the reaction mixture was recovered therefrom. Analysis of this reaction mixture by means of gas liquid chromatography and elementary analysis showed that there had been a 100% conversion of the olefins present in the hydrocarbon product stream from the dehydrogenation reactor along with a 54% selectivity to alkyldimethylamines in which the alkyl ranged from dodecyl to pentadecyl.

I claim as my invention:

1. A process for the preparation of an amine which comprises dehydrogenating a dehydrogenatable compound at dehydrogenating conditions in the presence of a dehydrogenating catalyst, treating the resultant product mixture in the absence of any separation with carbon monoxide, hydrogen and a nitrogen-containing compound in the presence of a catalyst comprising a rhodium- or ruthenium-containing compound at reaction conditions, and recovering the resultant amine.

2. The process as set forth in claim 1 in which said dehydrogenating conditions include a temperature in the range of from about 400° to about 700° C. and a pressure in the range of from about 0.1 to about 10 atmospheres.

3. The process as set forth in claim 1 in which said dehydrogenation is effected in the presence of hydrogen.

4. The process as set forth in claim 1 in which said dehydrogenation catalyst comprises a nonacidic complex containing a Group VIII noble metal and at least one metal selected from Groups IA and IIA and at least one element selected from Groups IVA, VA and VIIB of the Periodic Table composited on a porous carrier material.

5. The process as set forth in claim 4 in which said catalyst comprises platinum, lithium, and tin composited on alumina.

6. The process as set forth in claim 4 in which said catalyst comprises platinum, lithium, and arsenic composited on alumina.

7. The process as set forth in claim 4 in which said catalyst comprises platinum, magnesium and rhenium.

8. The process as set forth in claim 1 in which said dehydrogenatable compound is an aliphatic compound containing from 2 to about 30 carbon atoms/molecule.

9. The process as set forth in claim 8 in which said aliphatic compound is a normal paraffin containing from about 4 to about 30 carbon atoms/molecule.

10. The process as set forth in claim 1 in which said reaction conditions include a temperature in the range of from about 50° to about 350° C. and a pressure in the range of from about 10 to about 300 atmospheres.

11. The process as set forth in claim 1 in which said rhodium- or ruthenium-containing catalyst is selected from the group consisting of the metals, nitrates, halides, halocarbonyls and carbonyl of rhodium and ruthenium.

12. The process as set forth in claim 11 in which said catalyst is rhodium chloride.

13. The process as set forth in claim 11 in which said catalyst is chlorodicarbonylrhodium dimer.

14. The process as set forth in claim 11 in which said catalyst is ruthenium carbonyl.

15. The process as set forth in claim 1 in which said dehydrogenatable hydrocarbon is undecane, said nitrogen-containing compound is dimethylamine, and said amine is dodecyldimethylamine.

16. The process as set forth in claim 1 in which said dehydrogenatable hydrocarbon is henicosane, said nitrogen-containing compound is dimethylamine, and said amine is docosyldimethylamine.

17. The process as set forth in claim 1 in which said dehydrogenatable hydrocarbon is heptane, said nitrogen-containing compound is ammonia, and said amine is trioctylamine.

18. The process as set forth in claim 1 in which said dehydrogenatable hydrocarbon is undecane, said nitrogen-containing compound is aniline, and said amine is didodecylaniline.

* * * * *